United States Patent [19]

Gomm et al.

[11] 4,136,930
[45] Jan. 30, 1979

[54] METHOD AND APPARATUS FOR DETECTING FOREIGN PARTICLES IN FULL BEVERAGE CONTAINERS

[75] Inventors: Thiel Gomm, Castle Rock; Stephen E. Price, Lakewood, both of Colo.

[73] Assignee: The Coca-Cola Company, Atlanta, Ga.

[21] Appl. No.: 758,289

[22] Filed: Jan. 10, 1977

[51] Int. Cl.² ............... H04N 7/00; H04N 7/02
[52] U.S. Cl. .............................. 358/106; 358/105; 356/240; 250/223 B
[58] Field of Search ............... 358/101, 100, 105, 106; 250/555, 214 R, 563, 223 R, 223 B; 356/240, 197, 237

[56] References Cited

U.S. PATENT DOCUMENTS

| | | | |
|---|---|---|---|
| 2,798,605 | 7/1957 | Richards | 358/106 |
| 3,049,588 | 8/1962 | Barnett | 358/106 |

Primary Examiner—Robert L. Griffin
Assistant Examiner—Edward L. Coles

[57] ABSTRACT

A method and system for detecting foreign particles in the liquid of a full soft drink bottle are described. The bottle under inspection is first passed by a first electronic camera means which memorizes the optical characteristics of a bottle and the fluid contained therein and records these characteristics in the memory of a computer. The bottle under inspection is then rotated either about its vertical axis, or in a preferred embodiment about a horizontal axis to invert the bottle, and just after rotation is moved into the field of view of a second electronic camera means which records in the computer memory the image of the test bottle at this point in time. Any foreign particles within the bottle will tend to undergo movement due to the rotation or inversion of the bottle. Thus, the image detected by the second electronic camera will be different from the image detected by the first electronic camera and indicative of the presence of moving foreign particles within the bottle.

15 Claims, 12 Drawing Figures

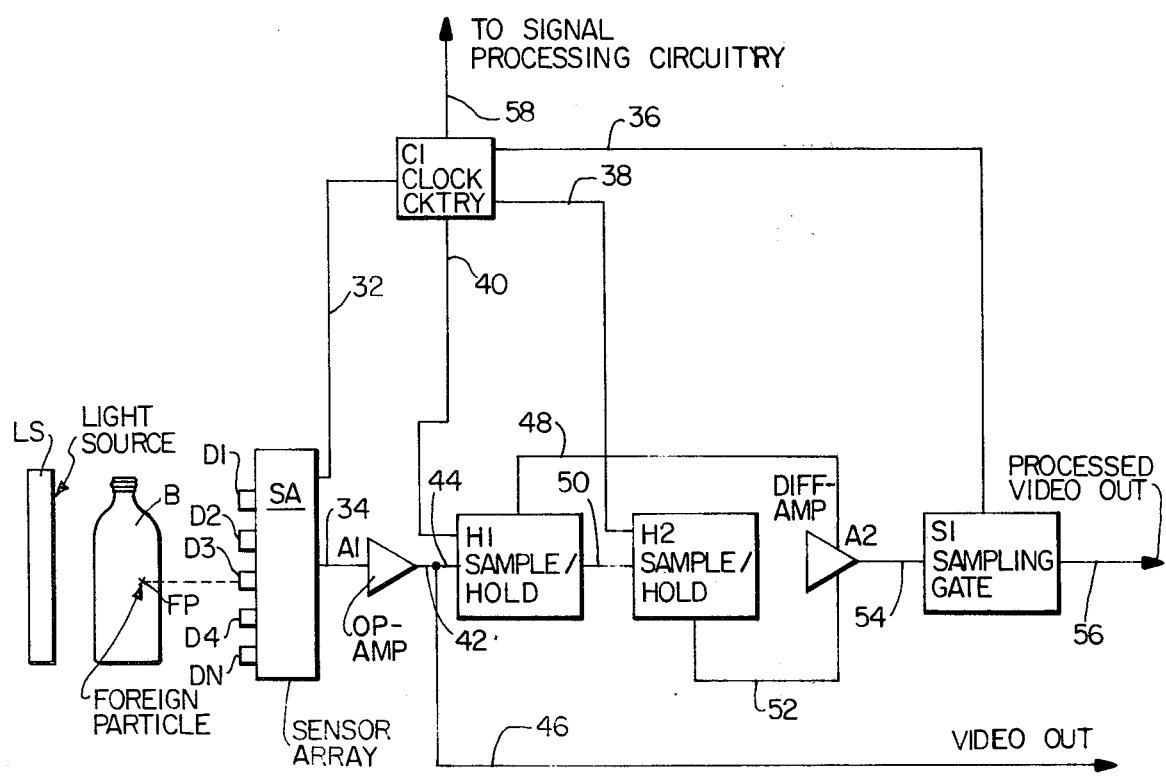
FIG. 2
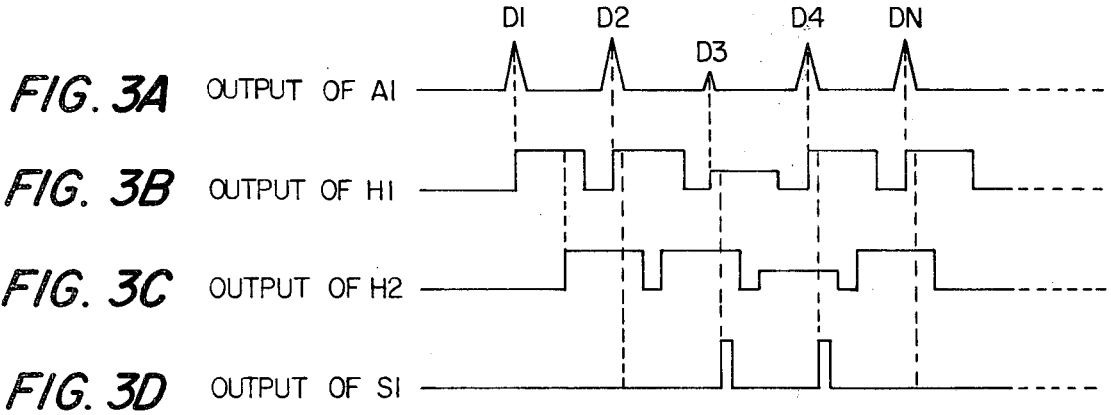
FIG. 3A OUTPUT OF A1
FIG. 3B OUTPUT OF H1
FIG. 3C OUTPUT OF H2
FIG. 3D OUTPUT OF S1

METHOD AND APPARATUS FOR DETECTING FOREIGN PARTICLES IN FULL BEVERAGE CONTAINERS

BACKGROUND OF THE INVENTION

1. Field of the Invention

The present invention relates to a method and system for detecting the presence of foreign particles within a fluid filled transparent bottle, such as a soft drink bottle. More specifically, the present invention relates to a system and method for detecting the presence of foreign particles within a bottle having distinctive optical characteristics in its side wall and distinctive logo printed thereon, which ordinarily would have the same effect on an optical detection system as a foreign particle disposed within the bottle.

2. Prior Art

Heretofore systems have been designed for detecting moving foreign particles within liquid filled containers. Systems of this type can be found in U.S. Pat. No. 3,598,907 to Drinkuth issued in August, 1971; U.S. Pat. No. 3,777,169 to Walter et al issued in December, 1973; and U.S. Pat. No. 3,765,533 to Stevenson et at issued in October, 1973. Each of the above patents disclose a system for detecting foreign particles within a liquid disposed in a container including:

means for swirling the liquid to generate movement of the particles;

video camera means for taking pictures of the bottle being inspected and liquids contained therein at first and second points in time;

means for storing the pictures taken at the respective times; and means for comparing the pictures stored in order to detect motion of the particles within the liquid, and thus their presence.

The systems of the above patents suffer from the following disadvantages. The prior art systems in the above patents utilize a video or analog sensing mechanism such as a conventional television camera. Thus, the inspection is generally accompanied by a surplus of generated data and is processed by such means as edge detection systems and supression systems.

In addition the systems of the above patents implement particle motion in the liquids by spinning the containers about their vertical axis rather than inverting the containers. Thus, light particles within the containers often are not agitated sufficiently to detect motion thereof.

The systems of the above patents suffer from the further disadvantage that all images of the article under inspection are recorded by a single camera device at a single station rather than recording the images in an in-line process wherein the first image is recorded at a first station on a rapidly moving conveyor and the second image is recorded at a second station on the rapidly moving conveyor. With the systems of the above patents, therefore, the object under inspection must remain for a considerable period of time at the inspection station in order to facilitate the recording of two images.

A further prior art patent of interest is U.S. Pat. No. 3,942,022 to Stumpf. The system of Stumpf discloses the use of a photodiode matrix array to detect movement of a light image. The Stumpf system detects motion by using a photodiode matrix array and scanning the output of the array at a time T and again scanning the output of the same array at a time delta T ($\Delta$ T). The results of the scan are then compared to indicate the presence of motion. The system disclosed in the Stumpf patent is not concerned with the high speed inspection of a plurality of containers moving along a conveyor.

Of additional interest with respect to prior art systems are U.S. Pat. No. 3,835,332 to Bridges issued in September, 1974 and U.S. Pat. No. 3,956,629 to Gomm issued in May, 1976. These patents are of interest in that they utilize a photodiode matrix array for inspecting an object for flaws wherein first and second images of the object are detected and compared, the first image being a reference standard for determining whether or not a defect exists in the object. However, in both of these patents the images compared are generated by the same camera and these patents are not concerned with high speed in-line inspection of containers.

Other U.S. Patents of interest which disclose the use of photodiode arrays for detecting flaws in objects are U.S. Pat. No. 3,886,356 to Gomm et al issued May, 1975 and U.S. Pat. No. 3,877,821 to Price et al issued April, 1975.

None of the above prior art patents disclose a system or method for suitably inspecting in rapid succession a plurality of transparent optically-irregular fluid-filled containers for the presence of foreign particles therein in a manner suitable for use with high speed soft drink filling equipment.

SUMMARY OF THE INVENTION

Accordingly, it is a primary object of the present invention to provide a high speed in-line filled bottle inspection system for detecting the presence of foreign particles within a container or bottle being inspected.

It is another object of the present invention to provide a method for generating foreign particle movement within a fluid in a container which adequately generates movement of both heavy and light foreign particles.

It is still another object of the present invention to provide an optical inspection system for liquid filled containers which can accurately inspect a container having irregularly shaped side walls, such as identifying logo or fluted side walls.

It is a further object of the present invention to provide a system for the high speed optical inspection of liquid filled containers wherein the data detected is in digital form and may be rapidly and efficiently processed by digital data processing means.

The objects of the present invention are fulfilled by providing a system for detecting foreign particles in an optically transparent liquid filled container including a first camera means disposed at a first station with respect to a rapidly moving conveyor for detecting a first optical image of a container moving along said conveyor when the fluid and foreign particles within the container are in a substantially static condition. The image detected by the first camera means is recorded in a memory for later comparison with a subsequently formed image of the bottle under different conditions. After the first image of the bottle and fluid therein is formed the bottle is agitated, such as by rotating or inverting the same about a horizontal axis passing therethrough, to generate motion of any foreign particles within the container. All of this is done in an in-line process while the container is being rapidly transported along a conveyor. A second optical camera means is disposed at a second station with respect to the conveyor and downstream of both the first camera and the container agitator means and is utilized to form a second image of the container after the foreign particles, if any are present, have been set into motion. The second optical image is also stored in the memory of a computer and the two optical images are then compared. Any difference in these two optical images beyond certain predetermined tolerances is an indication of the movement and thus the presence of a foreign particle within the fluid in the container.

If desired a third back-up camera may be provided to facilitate the detection of a foreign particle which might have been behind the logo on the side wall of the container when in the field of view of both the first and second cameras. The presence or use of a third camera increases the probability of detecting a foreign particle in a container and improves the reliability of the system of the present invention.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the present invention will become apparent to those skilled in the art from this detailed description.

BRIEF DESCRIPTION OF DRAWINGS

The present invention will become more fully understood from the detailed description given hereinbelow and the accompanying drawings which are given by way of illustration only, and thus are not limitative of the present invention and wherein.

FIG. 2 is a block diagram illustrating a preferred embodiment of the cameras utilized in the system of FIG. 1;

FIGS. 3A to 3D are timing diagrams illustrating the operation of the camera of FIG. 2;

DESCRIPTION OF PREFERRED EMBODIMENTS

Figure 1:
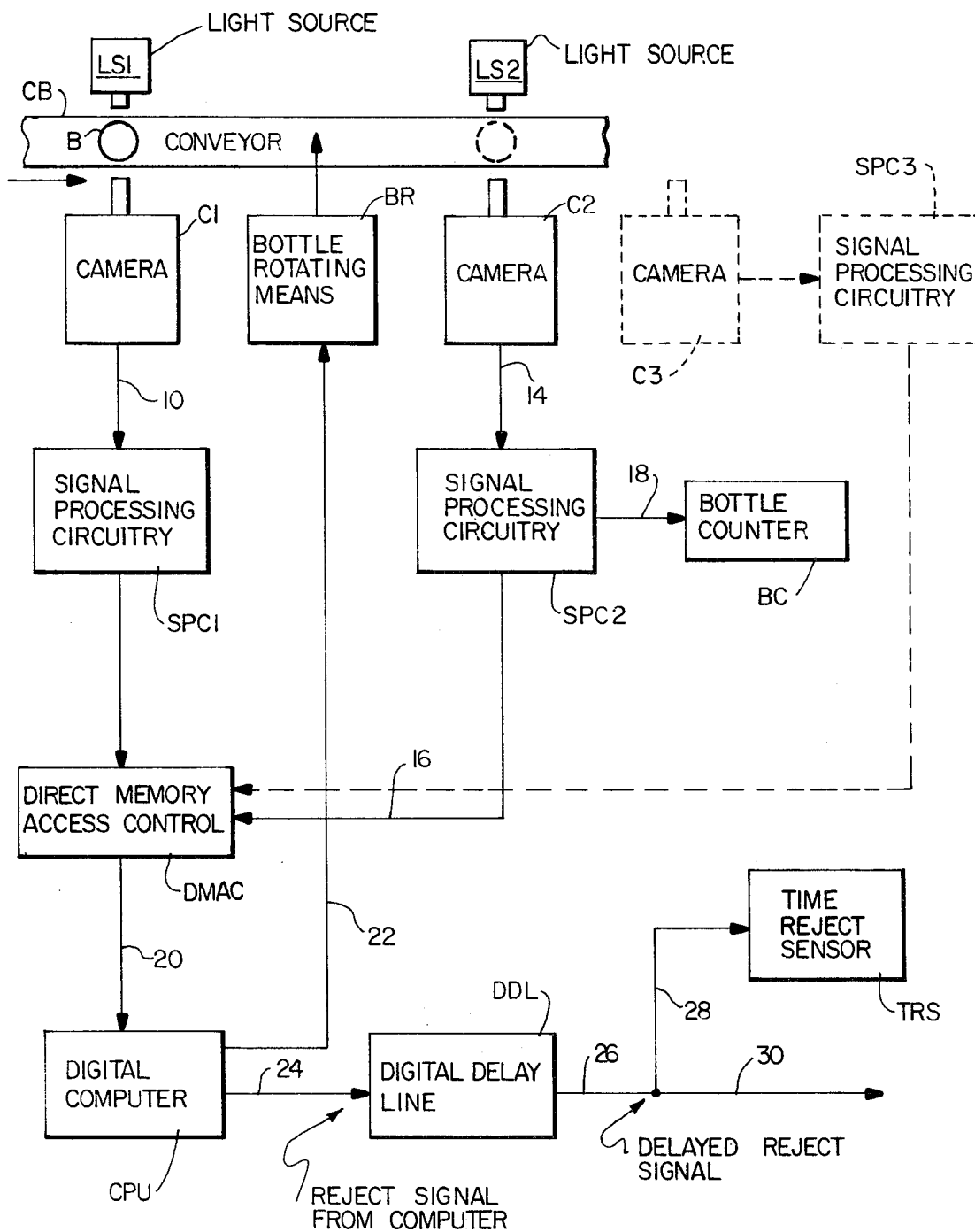
FIG. 1 is a block diagram of the overall bottle inspection system of the present invention.

Referring briefly to FIG. 1 there is illustrated a block diagram of the bottle inspection system of the present invention. As illustrated therein the bottle B being inspected and containing fluid, such as a soft drink and possible foreign particles therein, is transported along a conveyor CB. The bottle B passes sequentially between light source LS1 and camera C1; a bottle rotating means BR; light source LS2 and camera C2; a reject station (not shown); and an optional back-up camera C3.

In a manner to be more fully described hereinafter camera C1 in conjunction with computer CPU memorizes the optical characteristics of the bottle B which may be an optically tough soft drink bottle having fluted side walls and characteristic logo thereon. At this point on the conveyor the fluid in bottle B and any possible foreign particles are in a substantially static condition.

As bottle B continues down the conveyor CB from camera C1 it is engaged by bottle rotating means BR. Bottle rotating means BR may be any suitable means which agitates the liquid in bottle B and generates motion of foreign material. However, part of the present invention resides in the discovery that the most effective way to generate foreign particle movement in the liquid in bottle B is to turn bottle B upside down by rotating, the same 360° about a horizontal axis passing therethrough. It has been discovered in practicing the present invention, that when the bottle is rotated in this way by turning it upside down, both the light foreign particles (initially disposed at the top of the liquid in the bottle) and the heavy foreign particles (initially disposed at the bottom of the bottle) are displaced with equal effectiveness. Other types of apparatus or methods for generating particle movement in fluid filled bottles, such as in the prior art, employ means for rotating the bottle about its vertical axis to generate particle movement. These types of apparatus are not as effective as the method and apparatus of the present invention, for it is more difficult to generate detectable particle movement of small or light particles in these types of devices.

After the bottle B has been rotated at full 360° it is placed back on a conveyor by bottle rotating means BR and moves along the conveyor into registry with the optical system of camera C2. Camera C2 then scans the bottle B and through appropriate circuitry transmits the scanned image to digital computer CPU in a manner to be more fully described hereinafter with reference to FIGS. 2 to 4. In a preferred embodiment digital computer CPU is a Texas Instruments minicomputer, Model 960A.

Referring in more detail to FIG. 1, camera C1 is coupled to digital computer CPU through line 10 signal processing circuitry SPC1, line 12, direct memory access control DMAC, and line 20. In a like manner camera C2 is coupled to digital computer CPU through line 14, signal processing circuitry SPC2, line 16, direct memory access control DMAC, and line 20. Bottle rotating means BR is coupled to digital computer CPU through line 22 and receives control signals therethrough to initiate and terminate the operation of bottle rotating means BR in a suitable manner.

The system of FIG. 1 also includes other ancillary equipment to be described more fully hereinafter such as bottle counter BC coupled to signal processing circuitry SPC2 through line 18 and a digital delay line DDL connected to computer CPU via line 24. An output from digital delay line DDL is transmitted through line 26 and is applied to a rejection means (not shown) through line 30 and to a timed reject sensor TRS through line 28.

As illustrated in phantom, an optional back-up camera C3 and associated signal processing circuitry SPC3, may be provided to increase the probability of detecting of a given foreign particle. The operation of such a back-up camera will become more fully apparent hereinafter.

Figure 4:
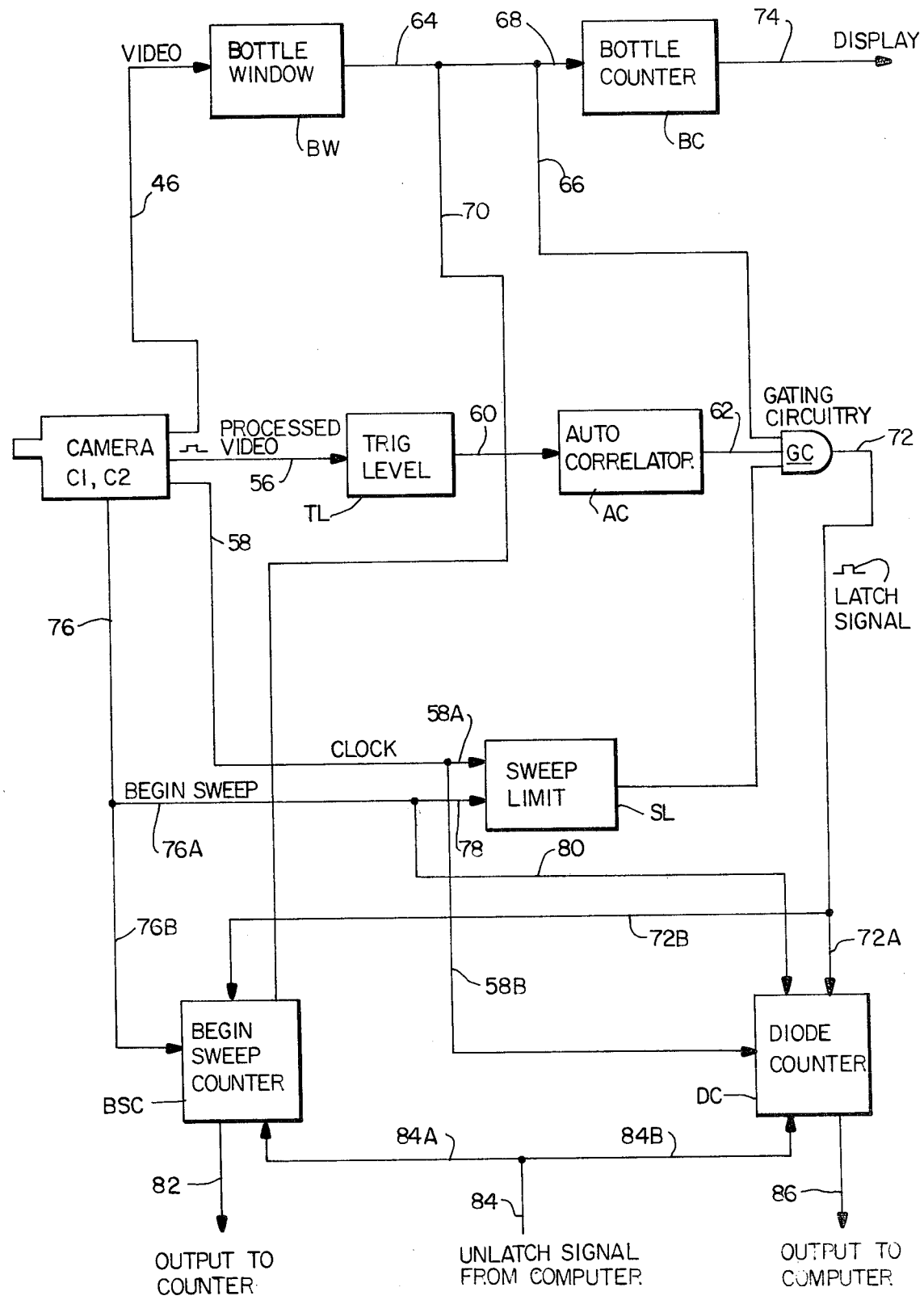
FIG. 4 is a block diagram illustrating the signal processing circuitry for the cameras of FIG. 1.
Figure 5A:
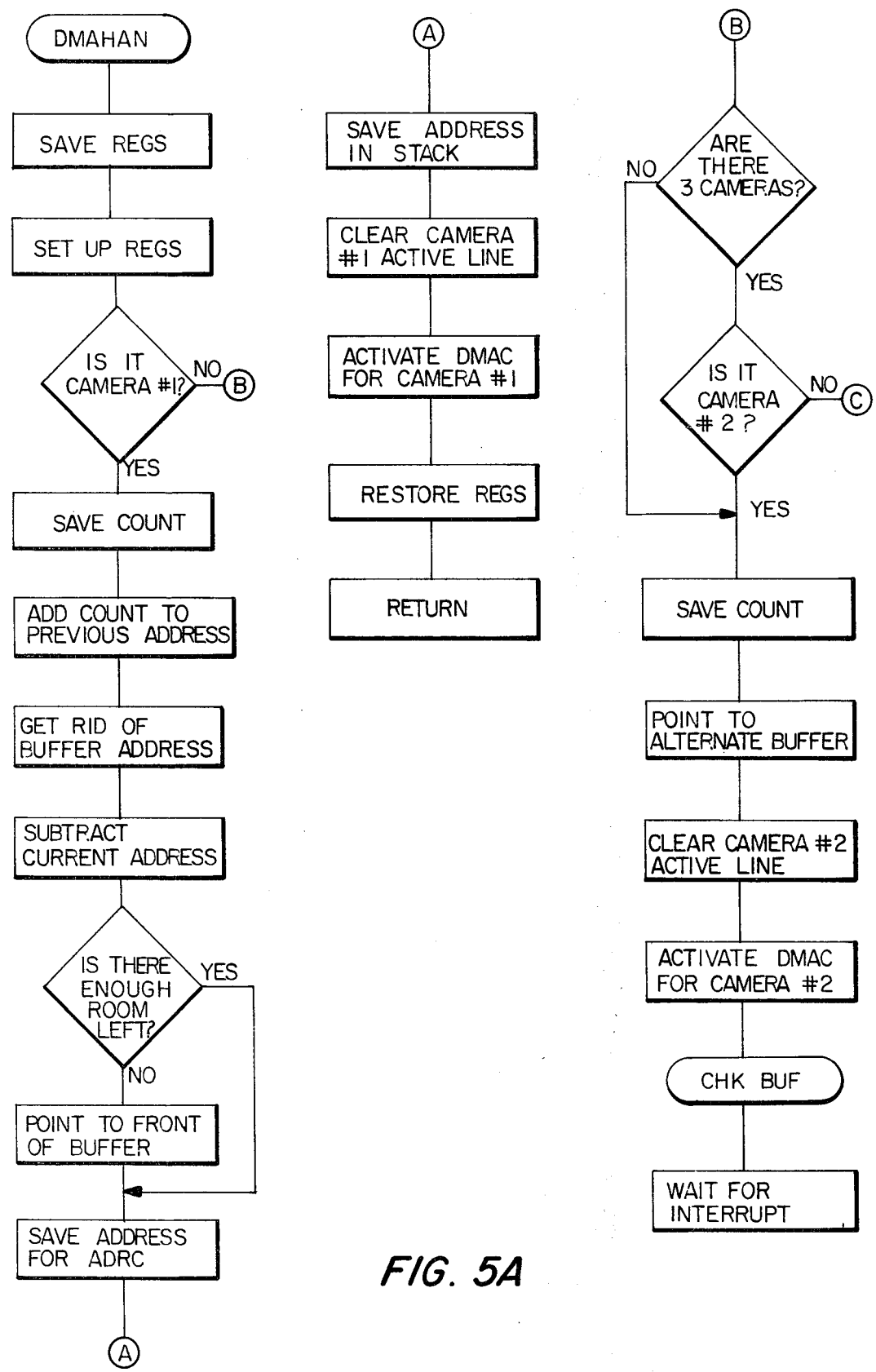
FIGS. 5A to 5E together form a flow chart illustrating the operation of the system of FIG. 1, as controlled by the computer program.
Figure 5B:
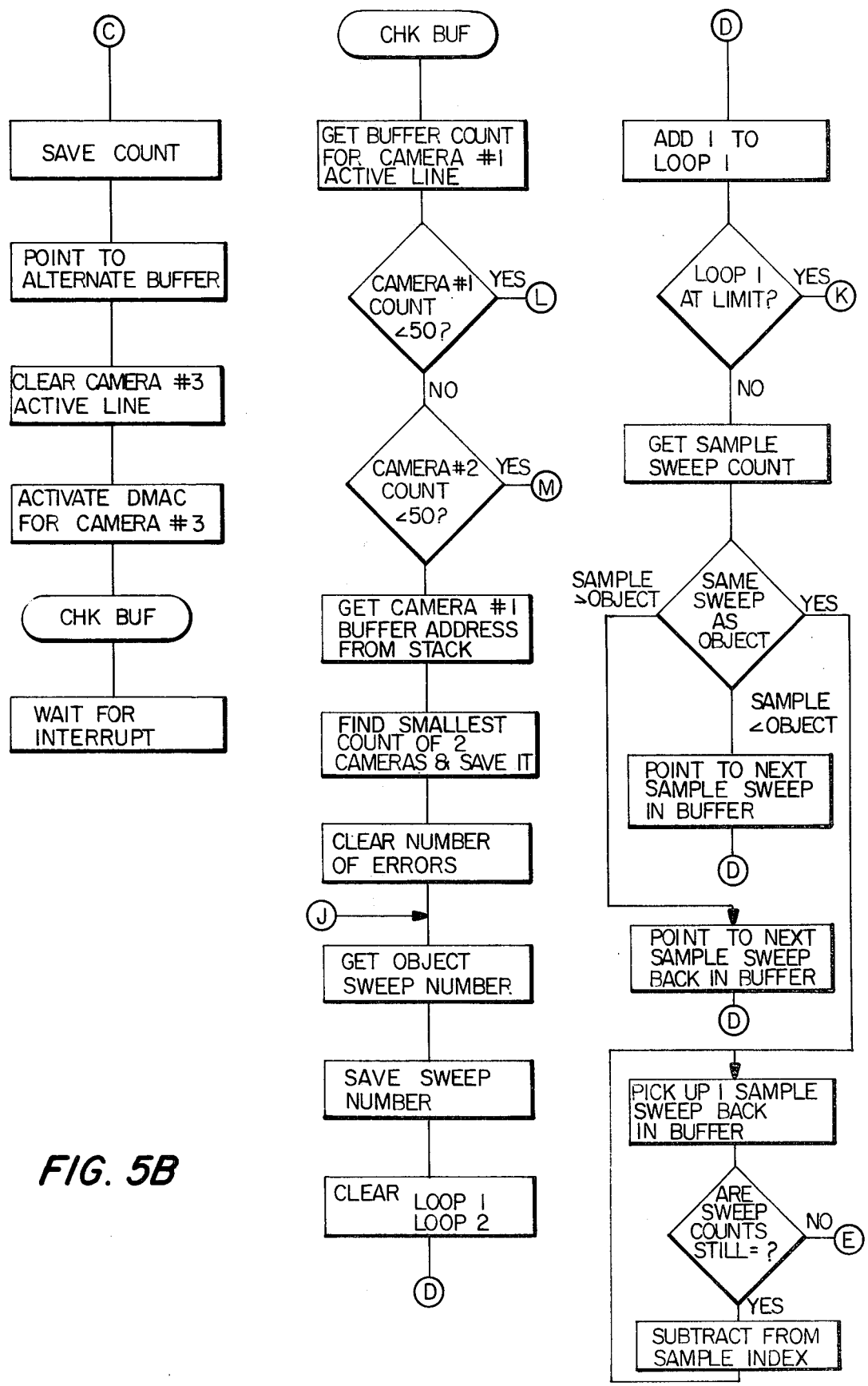
Figure 5C:
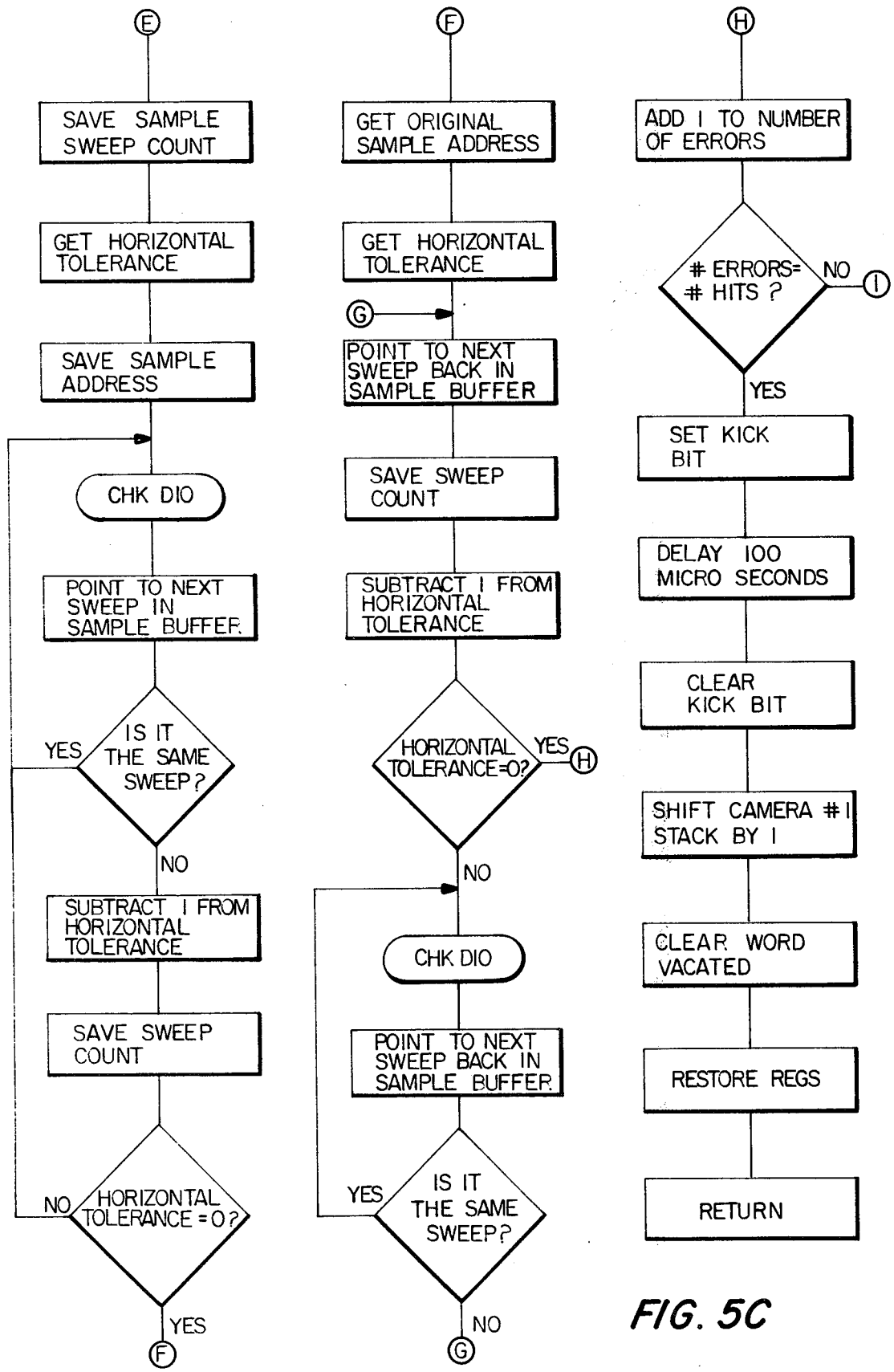
Figure 5D:
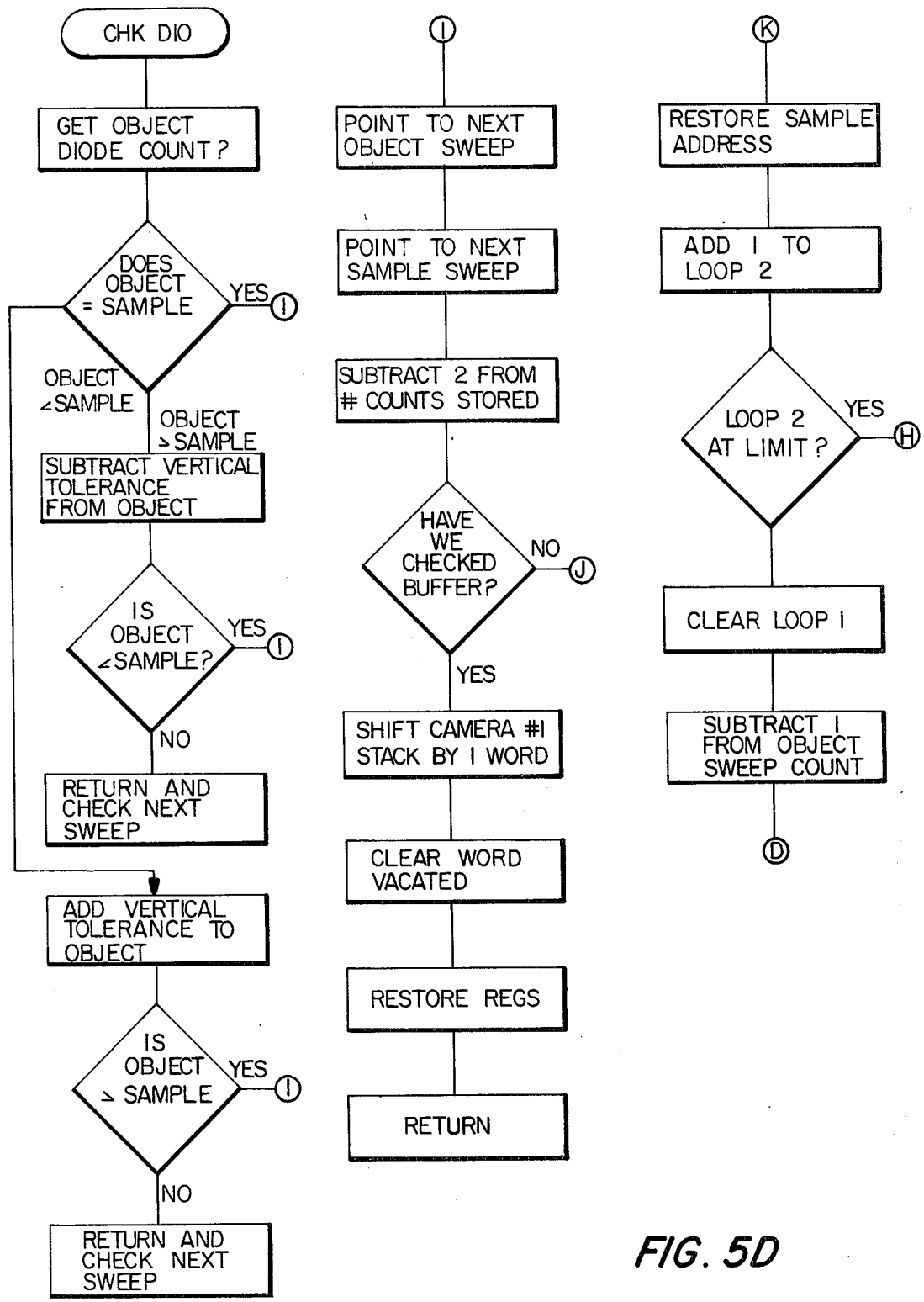
Figure 5E:
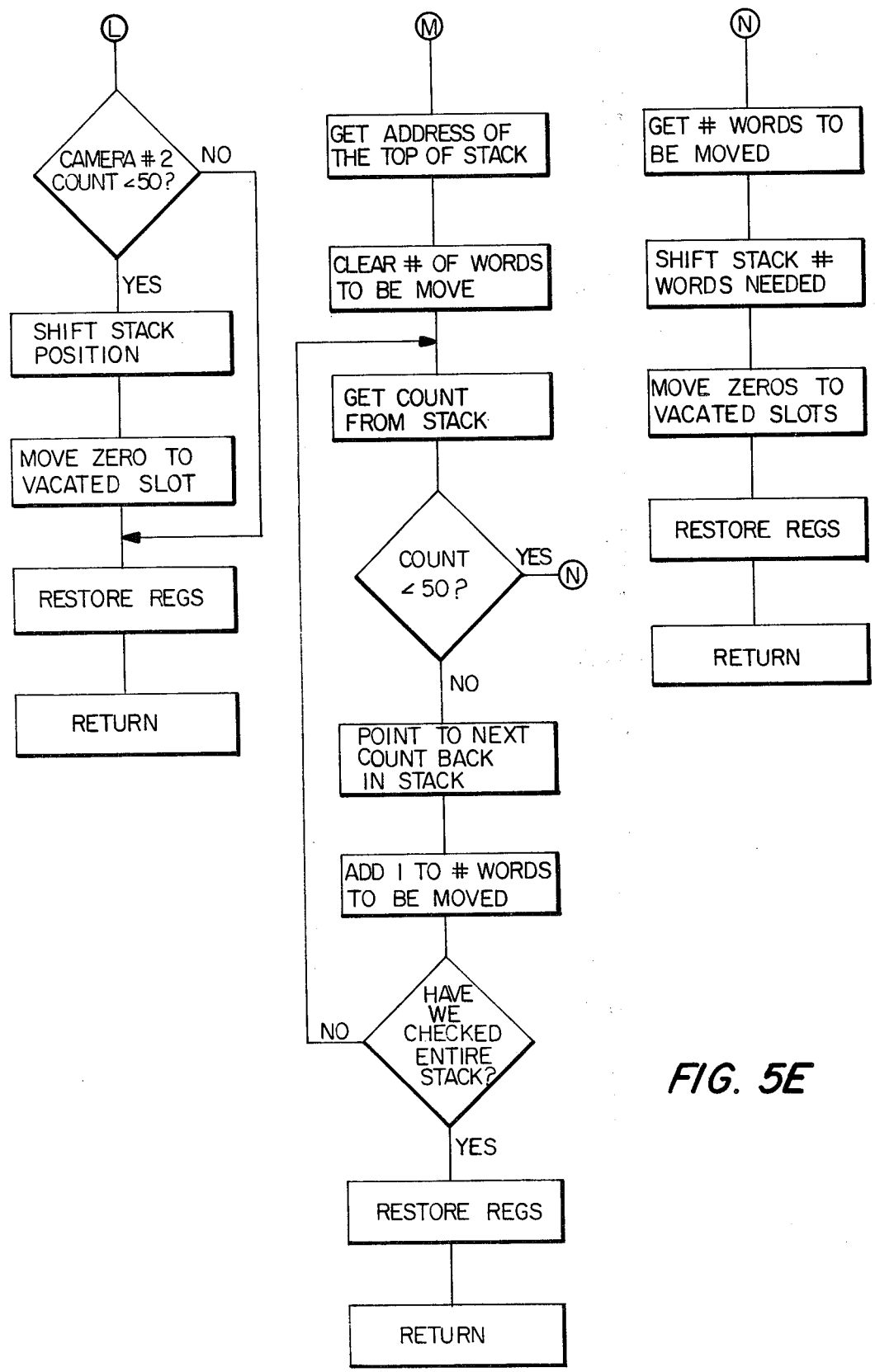

The details of the operation of the bottle inspection system of FIG. 1 will become more fully apparent hereinafter by reference to the details of the component parts of the respective cameras and the electronic processing circuitry as illustrated in FIGS. 2-4 to be described hereinafter.

PHOTODIODE INSPECTION CAMERAS C1, C2 and C3

Referring in detail to FIG. 2, there is illustrated a photodiode inspection camera and detection circuitry therefore suitable for use as inspection cameras C1, C2 and C3 in the system of FIG. 1. For the sake of simplicity, only one of such cameras is illustrated in FIG. 2 and the following explanation will refer to the operation of only one of said cameras as a bottle being inspected traverses its optical path. It should be understood, however, that at least two photodiode cameras and associated detection circuitry of the type illustrated in FIG. 2 are utilized in the preferred embodiment of the present invention.

Referring in detail to FIGS. 2, 3A, 3B, 3C and 3D there is illustrated a bottle B filled with a fluid such as a soft drink and containing a foreign particle such as FP. The bottle B is moving along a conveyor such a CO of FIG. 1 and as illustrated in FIG. 2, it would be moving substantially perpendicular to the plane of the drawing. A light source LS is provided which directs a substantially uniform or collimated beam of light through the bottle B and onto a photo-sensor array SA including an array of photodiodes D1 to DN as illustrated. For the sake of simplicity of explanation of the operation of the camera of FIG. 2, only one linear array of photodiodes D1–DN are illustrated. However, it should be understood that the sensor array SA in a preferred embodiment is comprised of a matrix of photodiodes.

As illustrated in the example of FIG. 2, the foreign particle FP is substantially aligned in the optical path between light source LS and diode D3 of the linear array. Accordingly, light transmitted through bottle B from light source LS will be attenuated by particle FP and diode D3 and, therefore, will receive less light than any of the remaining or surrounding diodes not in alignment with the particle FP.

Coupled to the output of sensor array SA by line 32 is clock circuitry C1. The clock circuitry C1 supplies a clock train to the sensing array SA, which causes the sensors in the sensing array SA to be serially interrogated. As each sensor or diode is individually interrogated, a corresponding pulse is supplied to the output of the sensing array SA via line 34. The amplitude of each output pulse is a function of the amount of light falling upon the individual photodiode or sensor being interrogated at that point in time. Thus, the output from the sensor array SA along line 34 comprises a pulse train, where the amplitude of each pulse is a function of the amount of light falling upon the photodiodes corresponding to that pulse. This pulse train is passed along line 44 to the input of an operational amplifier A1 and amplified.

The amplified output from OP amp A1 is illustrated in FIG. 3A and as can be seen in the timing diagram of 3A, the third pulse corresponding to the output from diode D3 is of less amplitude than the rest of the pulses. This pulse is of course of lower amplitude because of the foreign particle FP in the bottle under inspection blocks the light from light source LS which would ordinarily pass through the bottle B to diode D3.

The amplified output pulse train from amplifier A1 is transmitted directly through line 46 for purposes to be further explained hereinafter with reference to FIG. 4 and is also transmitted along line 44 to pulse detection circuitry including sample and hold circuitry H1, sample and hold circuitry H2, differential amplifier A2 and sampling gate S1. The function of H1, H2, A2 and S1, is to supply a pulse train through output line 56 where the amplitude of each pulse is a function of the difference in amplitude of the pulses outputted from amplifier A1. Thus, each pulse in the pulse train outputted from amplifier A1 is compared with its two adjacent pulses. Any difference in amplitude will be reflected as the amplitude of a pulse outputted from S1 along line 56.

Referring in more detail to the operation of this detection circuitry, the output of amplifier A1 is supplied to a sample and hold circuit H1 through line 44. The output of sample and hold circuit H1 may be seen in the timing diagram illustrated in FIG. 3D. As can be seen the amplitude of the incoming pulse is held by H1 for a period of time and is dumped by the clocking circuitry at point B in the timing diagram. The output of H1 is then transmitted through line 50 to a second sample and hold circuit H2. The timing of the sampling and dumping of H1 and H2 are controlled by the clocking circuitry from C1 through line 40 and 38, respectively. The phase relationship of the pulse waveforms of FIG. 3B and 3C are such that held pulses from H1 and H2 overlap. For example, the first pulse of H2 overlaps with the first pulse of H1. Accordingly, at a given point in time the amplitude of adjacent pulses originating as in FIG. 3A can be compared.

As can be seen in the timing diagram of FIG. 3A, the output from the first two sensors D1, D2 in the sensing array are of equal amplitude. It will be further noted in the timing diagram of FIG. 3A that the output pulses depicted correspond to the output pulses of diodes D1 to DN illustrated in FIG. 2. For example, the first pulse in timing diagram FIG. 3A corresponds to the first sensor D1, the second pulse corresponds to the second sensor D2, etc.

The outputs from sample and hold circuits H1 and H2 are supplied to the inputs of a difference amplifier through lines 48 and 52, respectively. The output of amplifier A2 will reflect any difference in voltage between the outputs of H1 and H2.

Referring to the timing diagrams of FIGS. 3B, 3C and 3D, it can be seen that at point D there is no difference in the amplitudes of the outputs of sample and hold circuits H1 and H2. Thus, at point D, the output of sampling gate S1 reflects or transmits no pulse along line 56. This is so because the amplitudes of the output pulses from H1 and H2, respectively, at point D are of equal amplitude because the first two pulses emerging from amplifier A1 (pulses from D1 and D2, respectively) along line 42 are of equal amplitude. Accordingly, when adjacent pulses emerging from the output of amplifier A1 are of equal amplitude, the output from sampling gate S1 is zero (0) indicating that the pulses compared, namely, the first two pulses D1, D2 emerging from the amplifier A1 are of the same magnitude.

The opposite result occurs when the third pulse emitted from amplifier A1 is compared with the preceding second pulse, since the third pulse is of lesser amplitude than the second pulse. This can be better understood by reference to point E in the timing diagram of FIGS. 3B–3D. As illustrated in FIGS. 3B, the amplitude of the output pulse from sample and hold circuit H1 at point E is of lesser amplitude than the corresponding point E in the output wave from sample and hold circuit H2. Accordingly, at this point in time, E, the output of amplifier A2, indicates the difference in the amplitude of the outputs of sample and hold circuits H1 and H2 and thus the outputs of diodes D2, D3. This difference in amplitude is represented by a pulse as illustrated in FIG. 3D which is passed via line 44 to sampling gate S1. The amplitude of this pulse reflects the differences in the outputs of sample and hold circuits H1 and H2 at point E in the timing diagram.

The fourth pulse in the pulse train of H1 is also of a higher amplitude than the preceding third pulse. Thus, the output of sample and hold circuit H1 corresponding to the fourth pulse is of a high amplitude at a point in time F and the output of sample and hold circuit H2 at the same point in time is of a low amplitude, reflecting the low amplitude of the third pulse D3 in the pulse train emitted from amplifier A1. At this point in time, F, the output of difference amplifier A2 will reflect a difference between the output of sample and hold circuit H1 and H2 and an additional pulse illustrated in FIG. 3 reflecting this difference will be outputted from sampling gate S1 along line 56.

The sampling performed by sampling gate S1 is controlled via line 36 by clock circuitry C1 to sample specific points in a timing relationship between H1 and H2. Thus, as can be seen, the processed video output transmitted along line 56 is a train of pulses whose amplitude is a function of the difference in amplitude of light radiation falling upon adjacent photodiodes or sensors in the sensing array SA.

As will become more readily apparent hereinafter, these pulses representing a difference in amplitude are indicative of the presence of a foreign particle in the fluid-filled bottle being inspected and the precise location of that foreign particle.

SIGNAL PROCESSING CIRCUITS SPC1, SPC2

The signal processing circuits SPC1, SPC2 of the system of FIG. 1 are illustrated in FIG. 3. It should be understood that only one camera and one signal processing circuit is illustrated in FIG. 3 for the sake of simplicity of explanation. However, at least two processing circuits such as illustrated in FIG. 3 are provided, one for each of the cameras C1 and C2. These processing circuits process the signals from a camera of the type described in FIG. 2 in a manner to be more fully understood from the following description.

As an article is placed in the viewing area of the camera C1 or C2, the camera will scan the container. If there are any abrupt changes in the light, transmitting or reflecting characteristics of the container that may be caused by a foreign particle in the fluid-filled container, the camera C1 or C2 will output a pulse from the processed video output along line 56 as explained hereinabove with reference to FIG. 2. The amplitude of this pulse transmitted along line 56 is a function of the abruptness in change of optical characteristics of the article at a given point.

This pulse is passed to a trigger level circuit TL that ignores all pulses below a specific amplitude. The output of the trigger level circuit is supplied through line 60 to an autocorrelator AC. In order for the signal pulse to pass through the autocorrelator AC, it is necessary that the camera output a pulse in approximately the same position on two consecutive sweeps. The function of the autocorrelator is to cause the processing circuitry in the system to ignore any noise spikes or very small anomalies in the container under inspection. The signal from the autocorrelator is next passed through line 62 to a gating circuit GC. A sweep limit circuitry SL is provided to receive the camera clock signal via lines 58, 58A and sets the limits of the scan on the article under inspection. In order for a signal on line 62 to be passed through the gating circuit, it must be within the sweep limits. These limits are adjustable such as by thumbwheel switches or other means (not shown).

A bottle window circuitry BW is provided for receiving the video output from the camera along line 46 of FIG. 2. When the entire video signal (pulse train in FIG. 3A) from the camera lessens in amplitude, this indicates that an article or container is in the viewing area of the camera. When an article is in the camera viewing area, the bottle window circuit BW will supply a conditioning level to the gating circuit GC along lines 64, 66. When the bottle window circuit BW is supplying a conditioning level to the gating circuit GC, a signal coming from the autocorrelator AC will be passed through gate GC to line 72. Once the signal is passed through the gating circuit GC, (from hereon for the purposes of explanation) it will be referred to as a latch signal. Once it is passed through the gating circuit GC, it is considered as an anomaly, such as a foreign particle, in the container under inspection.

The clock signal from the camera is also supplied along lines 58, 58B to diode counter DC. DC is referred to as a diode counter, since the camera sensing array SA is a matrix of diodes in the preferred embodiment of the present invention. However, it should be understood that DC is also capable of operation with any other selected form of sensing array SA. In operation each clock pulse transmitted via lines 58, 58B corresponds with the interrogation of one diode in the matrix SA. Although the sensing array SA in FIG. 2 is a matrix of diodes, it should be understood that other forms of photosensors may be used without departing from the spirit and scope of the present invention.

The diode counter DC is reset by a begin sweep signal which also comes from the camera via lines 76, 76A. The begin sweep signal is a control pulse that indicates the camera has started a new scan. As the diode counter DW receives each clock pulse from the camera along line 58B, it will increment by one. Thus after the diode counter DC has received the first clock pulse and it is incremented to the number one, this indicates that one diode has been interrogated. Should the diode counter DC be incremented to the number 100, that count would indicate that the 100th diode had just been interrogated. When the diode counter DC receives a latch signal from line 72, whatever number the diode counter had been incremented to at that time will be latched at the output of the counter DC onto line 86, even though the counter itself continues to increment with the camera clocks. This latched count is passed along line 86 to the computer. In return the computer will send an unlatch signal via lines 84, 84B in order to unlatch the diode counter DC after the computer has placed the latched count in the memory. Of course now the diode counter DC is ready for a new latch signal should another anomaly occur in the article under inspection.

A begin sweep counter BSC is provided and operates in much the same manner as the diode counter. However, instead of counting the individual sensors in one row in the sensing array SA, the begin sweep counter counts the row number being scanned by the camera. The begin sweep counter is reset at the end of the bottle window through line 70. Thus, the begin sweep counter BSC will continue to increment with each begin sweep pulse until the article under inspection is passed from view. The begin sweep counter is also unlatched by the computer by an unlatch signal transmitted via lines 84, 84A after the computer has had time to place the information in the memory. Thus, it can be seen that when a signal has passed the gating circuitry GC and is considered to be an anomaly in the article under inspection, the computer will receive both the diode count in each horizontal row of the matrix and the sweep count identifying the row being scanned at the given instance of the occurence of an optical anomaly in the article under inspection. Thus, the computer has received a vertical and horizontal designation of the location of the anomalies seen by the inspection camera.

The bottle counter BC receives one count for each bottle window via lines 64, 68. Thus, the count in the bottle counter at any given time is the number of bottles that have passed the camera. This count may be passed along line 74 to a display.

SYSTEM OPERATION OF FIG. 1

The system operation can be readily understood by again referring to FIG. 1.

As the bottle passes through the viewing area of camera C1, the signal processing circuitry SPC1 passes the diode count and the sweep count of any optical anomalies to the direct memory access controller. (See signal processing circuitry of FIG. 4). The direct memory access control DMAC places the diode count and the sweep count of each anomaly into the memory of the digital computer CPU. Thus after a bottle has passed through the viewing area of camera C1 the computer contains a matrix of numbers. This matrix pin points the location, both horizontally and vertically of each anomaly in the bottle, as described hereinbefore. After the bottle has left the viewing area of camera C1 and entered the viewing area of camera C2 the signal processing circuitry SPC2 for camera C2 performs the identical task that the signal processing circuitry SPC1 for camera C1 performed. Thus, the computer CPU will contain a matrix of all of the anomalies in the bottle B as viewed by camera C1, and a matrix of all of the anomalies in the bottles viewed by camera C2. These two matrices will be compared by the computer CPU and, if they are not identical within specified tolerances, the bottle B will be considered to contain foreign material and will be rejected. Thus, it is necessary that between camera C1 and camera C2, the bottle be rotated or turned in some manner such as by bottle rotating means BR to displace any foreign material in the soft drink. Should there be foreign material in the soft drink, and as it passes camera C2 this foreign material that has been displaced from the position that it was in when it passed camera C1, the two matrices in the computer will not be identical and the bottle will be rejected.

When a reject signal is generated by the computer the reject signal is supplied along line 24 to a digital delay line DDL which will delay the reject signal issued at 30. This allows the bottle to pass down the conveyor belt CB until it reaches a suitable reject mechanism before being rejected.

The Timed Reject Sensor TRS is a circuit that will indicate if no bottles have been rejected within a specified period of time. The purpose of this sensor is to check on the inspection system to insure that it has not ceased to operate and reject faulty bottles.

A belt speed monitor may be provided which receives a signal from the conveyor system that indicates the speed of the conveyor belt. This signal may come from a mechanical device or a device such as a photosensor. This signal that indicates the speed of the conveyor belt is supplied to the computer. Thus, the computer can make necessary compensations for changes in the speed of the conveyor belt.

The bottle counter BC receives a signal from the signal processing circuitry from one of the cameras C1 or C2. The bottle counter receives one count for each bottle that has passed the camera, thus, the display of the bottle counter indicates how many bottles have passed the camera.

The Direct Memory Access Channel (DMAC) Handler of FIG. 1 contains the components necessary to implement the filled bottle inspector program. Any commercially available program controller may be utilized as the DMAC. Within the DMAC Handler are the instructions (DMAHAN) needed to keep track of the bottles (in relation to Camera C1 and Camera C2). The routine to examine the differences between the views from the two cameras is also in the DMAHAN routine. An explanation of data handling from the time a bottle comes into view until it is either passed or rejected by the system follows.

A bottle comes into the view of camera C1. During the time the bottle is in view, the DMAC Interface sends data to sequential memory locations in the CPU starting at an address furnished by the program. The data is in the form of:

a. 16 bit binary sweep count which represents the sweep location of the perturbation (count stored in BSC of FIG. 4).

b. 16 bit binary diode count which represents the diode location of the perturbation (count stored in DC of FIG. 4).

As the bottle goes out of view of Camera C1, a interrupt signal is issued to the computer from DMAC. When this interrupt signal is issued the program (DMAHAN) is implemented.

Upon implementing the program (DMAHAN), the camera that caused the interrupt signal is identified. If it is camera C1 that is interrupting, the address of the data is added to an Address Stack of the CPU. Within the Address Stack are the addresses of bottle information for all bottles between camera C1 and camera C2. After the data has been saved, in the stack a new address is issued to the DMAC interface for the next bottle. The existing interrupt is cleared and interrupts are enabled to wait for the next interrupt.

If camera C2 is interrupting, the alternate buffer address is given to the DMAC interface. Processing of the bottle is then begun. The camera C1 address for that specific bottle is picked up from the address stack. The bottle is then checked (camera C1 buffer vs camera C2 buffer) for differences in diode and sweep count beyond the predetermined tolerance settings. If sufficient differences occur to warrant rejecting the bottle, a kick or reject command is issued from the CPU. Otherwise, the bottle is allowed to pass.

A more detailed explanation of the program implemented by the DMAC may be obtained by reference to the flow chart of FIGS. 5A to 5D which is believed to be self explanatory to one of ordinary skill in the art.

The system disclosed herein may be modified as would occur to one of ordinary skill in the art without departing from the spirit and scope of the present invention.

For example, the system of the present invention illustrated in FIG. 1 may be further provided with a third camera C3 (shown in phantom) disposed downstream of the conveyor CB. The third camera is a backup camera, the purpose of which is to enable the system to see a higher number of foreign particles. For example, if cameras C1 and C2 observe a bottle when a particle is behind the logo on the bottle, the particle would go undetected. However, it is highly improbable that the particle would still be behind the logo when observed by camera C3. Thus, the third camera increases the safety and integrity of the system.

The electronic components of the circuits of the present invention may be commercially available integrated circuit chips, the selection of such chips being well within the skill of the routineer in conjunction with the foregoing disclosure.

The system of the present invention may be utilized to perform additional inspection functions by suitably programing the computer. For example, the system may be utilized for at least the following additional functions: detecting proper fill levels of containers; detecting the proper content of pallets or cases for warehouse control; container identification; bottle sorting; and other optical comparisons.

The containers being inspected by the apparatus of the present invention may be any form of transparent container such as glass or plastic soft drink bottles.

What is claimed is:

1. A method of detecting the presence of foreign particles in a liquid-filled optically transparent container comprising the steps of:
   a. detecting a first optical image of said container when the fluid and foreign particles therein are in a substantially static condition;
   b. storing said optical characteristics of said container containing said substantially static fluid in a memory;
   c. rotating said container about a horizontal axis passing through said container to generate both heavy and light foreign particle movement in the fluid therein;
   d. detecting a second optical image of said container after the container has been rotated;
   e. storing said second optical image in a memory; and
   f. comparing said first and second optical images of said container to determine a predetermined degree of difference between said images indicative of the presence of moving foreign particles in the fluid in said container.

2. The method of claim 1 including the further step of generating a reject signal for said container when said first and second images possess said predetermined degree of difference.

3. The method of claim 1 wherein said rotating step is effected by rotating said container 360 degrees about said horizontal axis.

4. The method of claim 1 wherein a plurality of said containers are moving in-line along a conveyor means, said first optical image is detected at a first station along said conveyor means, said second optical image is detected at a second station along said conveyor means, and said step of rotating is performed between said first and second stations.

5. A system for detecting foreign particles in an optically-transparent liquid-filled container comprising:
   a. conveyor means for transporting a plurality of said containers in seriatum through at least first and second inspection stations;
   b. first camera means disposed at said first station for detecting a first optical image of each of said containers when the fluid and foreign particles therein are in a substantially static condition;
   c. means for storing said first image in a memory;
   d. agitation means disposed between said first and second stations for generating motion of said foreign particles in said fluid-filled containers;
   e. second camera means disposed at said second station for detecting a second optical image of said container after said foreign particles have been set into motion;
   f. means for storing said second optical image in a memory;
   g. means for comparing said first and second images stored in said memories; and
   h. means responsive to said means for comparing for generating a reject signal when said first and second optical images differ by a predetermined degree.

6. The system of claim 5, wherein there is further provided a third camera means disposed at a third station; means for storing an optical image of said third camera means, and means for comparing the optical image of said third camera means with the optical image of said first camera means.

7. The system of claim 5 further including means for monitoring the frequency of occurrence of said reject signal.

8. The system of claim 5 further including means for displaying the number of containers which have been inspected by the camera means.

9. The system of claim 5 wherein said first and second camera means comprise a radiation source directed toward said containers on said conveyor means and an array of photosensors for receiving radiation from said source which passes through said container means.

10. The system of claim 9 wherein said array of photosensors is a matrix of photodiodes.

11. The system of claim 5 wherein said agitation means comprises:
    means for rotating said containers about a horizontal axis passing therethrough.

12. The system of claim 11 wherein said means for rotating includes, means for rotating said containers 360 degrees about said horizontal axis while said containers are disposed between said first and second stations.

13. A system for detecting the presence of foreign particles in a liquid-filled optically transparent container comprising:
    means for detecting a first optical image of said container when the fluid and foreign particles therein are in a substantially static condition;
    memory means for storing said optical characteristics of said container containing said substantially static fluid;
    means for rotating said container about a horizontal axis passing through said container to generate both heavy and light foreign particle movement in the fluid therein;
    means for detecting a second optical image of said container after the container has been rotated;
    memory means for storing said second optical image; and
    means for comparing said first and second optical images of said container to determine a predetermined degree of difference between said images indicative of the presence of moving foreign particles in the fluid in said container.

14. The system of claim 13 further including means for generating a reject signal for said container when said first and second images possess said predetermined degree of difference.

15. The system of claim 13, wherein said means for rotating rotates said container 360 degrees about said horizontal axis.

* * * * *